(12) United States Patent
Gatzemeyer et al.

(10) Patent No.: US 7,784,136 B2
(45) Date of Patent: *Aug. 31, 2010

(54) TOOTHBRUSH WITH KINETIC PLATE

(75) Inventors: John J. Gatzemeyer, Hillsborough, NJ (US); Eduardo J. Jimenez, Manalapan, NJ (US); Eyal Eliav, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/241,592

(22) Filed: Sep. 30, 2008

(65) Prior Publication Data

US 2009/0025157 A1    Jan. 29, 2009

Related U.S. Application Data

(60) Division of application No. 11/563,475, filed on Nov. 27, 2006, now Pat. No. 7,448,108, which is a continuation of application No. 10/260,585, filed on Sep. 27, 2002, now Pat. No. 7,140,058.

(51) Int. Cl.
   *A61C 17/22* (2006.01)
(52) U.S. Cl. ............................. 15/22.1; 15/28
(58) Field of Classification Search .................. 15/22.1, 15/22.2, 22.4, 28
   See application file for complete search history.

(56) References Cited

U.S. PATENT DOCUMENTS

| | | | |
|---|---|---|---|
| 2,206,726 A | 7/1940 | Lasater | |
| 4,368,272 A | 1/1983 | Kashket | |
| 5,353,460 A | 10/1994 | Bauman | |
| 5,524,312 A | 6/1996 | Tan et al. | |
| 5,617,603 A | 4/1997 | Mei | |
| 5,625,916 A | 5/1997 | McDougall | |
| 5,628,082 A | 5/1997 | Moskovich | |
| 6,000,083 A | 12/1999 | Blaustein et al. | |
| 6,446,295 B1 | 9/2002 | Calabrese | |
| 6,785,929 B2 | 9/2004 | Fritsch et al. | |
| 2001/0020314 A1 | 9/2001 | Calabrese | |
| 2001/0023516 A1 | 9/2001 | Driesen et al. | |
| 2003/0066145 A1 | 4/2003 | Prineppi | |

(Continued)

FOREIGN PATENT DOCUMENTS

GB    2319170    5/1998

(Continued)

*Primary Examiner*—Mark Spisich
(74) *Attorney, Agent, or Firm*—Amy M. Fernandez

(57) ABSTRACT

A powered toothbrush is provided and includes a handle portion having a neck formed at one end and a head coupled to neck. The head includes a first carrier that is coupled to the head and is operatively connected to a first drive for moving the first carrier in a first direction. The first carrier has bristles, elastomeric cleaning members, or a combination thereof extending outwardly therefrom. The head also includes a second carrier that is coupled to the head and is in selective engagement with a protrusion extending in a recess defined by the first carrier to impart movement in a second direction. The second carrier has bristles, elastomeric cleaning members or a combination thereof extending outwardly therefrom. In an exemplary embodiment, the first carrier oscillates in a rotational direction and the second carrier moves in a direction parallel to the head.

19 Claims, 16 Drawing Sheets

U.S. PATENT DOCUMENTS

| | | |
|---|---|---|
| 2003/0084524 A1 | 5/2003 | Blaustein et al. |
| 2003/0084525 A1 | 5/2003 | Blaustein et al. |
| 2003/0140437 A1 | 7/2003 | Eliav et al. |
| 2004/0143917 A1 | 7/2004 | Ek |

FOREIGN PATENT DOCUMENTS

| | | |
|---|---|---|
| JP | 9-140456 | 6/1997 |

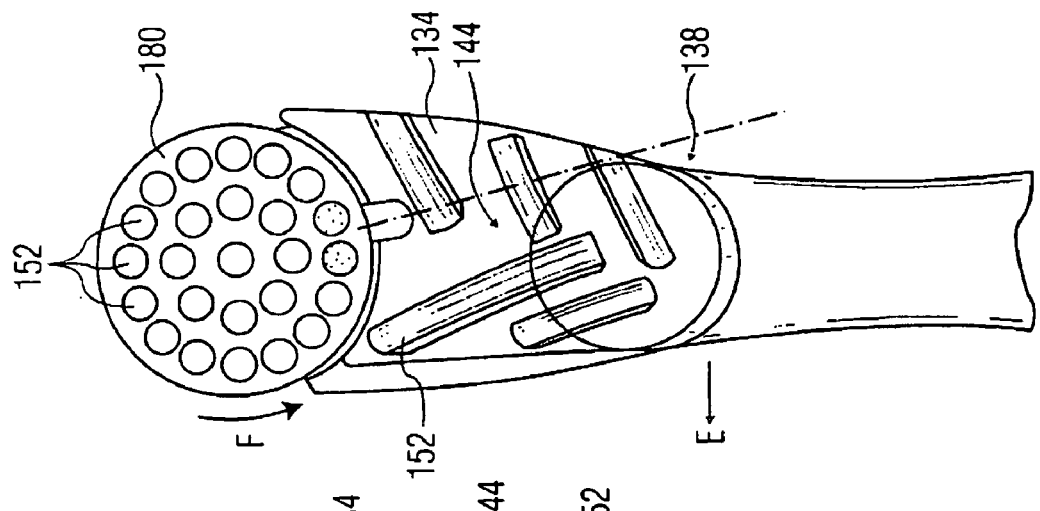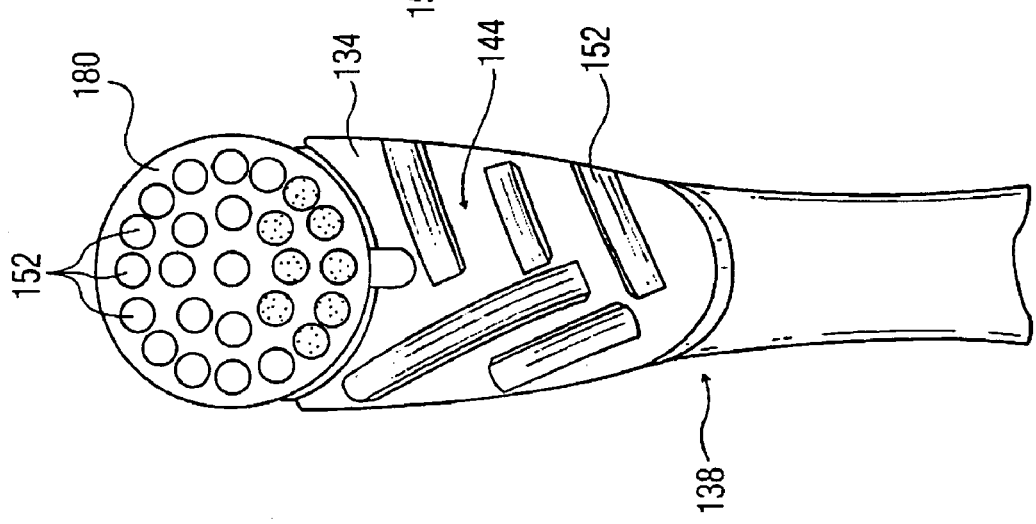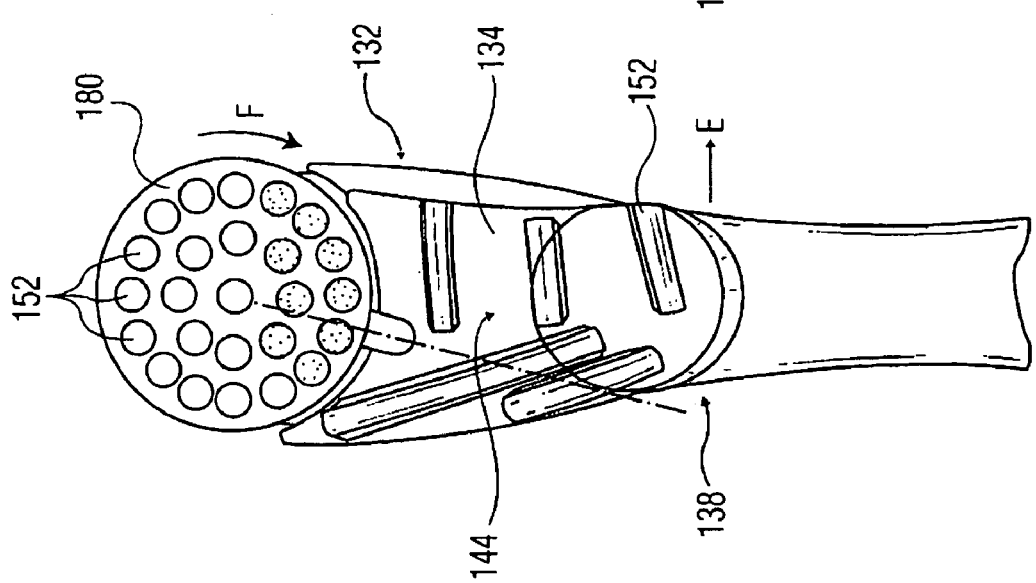

TOOTHBRUSH WITH KINETIC PLATE

CROSS-REFERENCE TO RELATED APPLICATIONS

This application is a divisional of U.S. patent application Ser. No. 11/563,475, filed Nov. 27, 2006, now U.S. Pat. No. 7,448,108, which is a continuation application of U.S. patent application Ser. No. 10/260,585 filed Sep. 27, 2002, now U.S. Pat. No. 7,140,058.

BACKGROUND OF THE INVENTION

1. Field of the Invention

The present invention relates to powered toothbrushes, and more particularly, to a toothbrush having a head with two distinct moving sections that each provide oral health benefits to the user.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of toothbrush by the user, provide superior cleaning than manual toothbrushes. Typically, powered toothbrushes are powered by disposable or rechargeable batteries that power an electric motor that in turn drives toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat, concave, or convex. The more precise conformation between the bristles and the tooth surface, the more effective toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. Toothbrush shown in McDougall has a disc-shaped bristle carrier. The bristle carrier, and thus the bristles, are driven in a vibrating or oscillating manner. This type of toothbrush is described herein with reference to FIGS. 1A-1C. A toothbrush 5 includes a handle portion 10 at a proximal end of toothbrush 5 and a head 11 at a distal end of toothbrush 5. Handle portion 10 has compartments for containing a powered motor 14 and batteries 15 and 16. Head 11 includes a generally circular bristle holder (carrier) 13. A rotatable shaft 12 extends from the motor 14 to head 11. A shaft coupling 17 may be located along the shaft 12 and configured to provide for the shaft 12 to be separated at a point between the motor 14 and head 11. This permits the shaft to be removed from toothbrush 5, e.g., for cleaning, servicing, or replacement.

Head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. Providing a rotating or oscillating bristle holder (carrier) with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations associated with a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of Blaustein et al. is that the static bristle section provides no better cleaning, whitening or stimulation than a manual toothbrush.

International Application No. PCT/EPO1/07615 of Braun GmbH discloses a powered toothbrush with two separate bristle parts that can move. Each bristle part can have a different range and/or type of motion. However, only one bristle part is powered. The other unpowered bristle part moves due to a resonance effect imparted by the frequency of the movement of the first bristle part.

This free resonance causes a number of difficulties. First, because any contact between the bristle parts will dampen or cancel any resonance of the unpowered bristle part, the unpowered bristle part "floats" separately from the powered bristle part. This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles or bristles that are otherwise movable. There is also a need for a toothbrush having increased whitening and/or stimulation than known toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and either a fixed head or a linkage for receiving a removable head at a distal end thereof. A neck is further formed between handle portion and head. According to one embodiment of the invention, the head includes two distinct movable parts that each and together provide oral health benefits, each being adapted to have a number of bristles or elastomeric cleaning members extending therefrom adapted to contact surfaces of one or more teeth and surrounding areas. The powered toothbrush is further formed with a drive mechanism that imparts movement to the first movable part to deliver a cleaning, polishing, whitening action that supplements the cleaning efficiency of a typical powered toothbrush. The first movable part in turn imparts movement to the second movable part.

In one embodiment, the first movable head part is a first bristle carrier that supports a number of bristle tufts, elastomeric cleaning members, or a combination thereof. The first bristle carrier is operatively mounted to head and is coupled to the drive mechanism such that the first bristle carrier oscillates back and forth in a direction parallel to toothbrush head. Preferably, the oscillating first bristle carrier is moved back and forth in a rotational direction. The second movable part is formed as a second carrier that includes an elastomeric platform that is operatively fixedly mounted at at least one portion thereof to the head and is selectively engaged by the first carrier to provide movement. The second carrier thus oscillates and translates in a direction parallel and longitudinal to the head, thereby providing a moving head section in addition to the oscillating section that is formed by the first bristle carrier.

Other features and advantages of the present invention will be apparent from the foregoing detailed description when read in conjunction with the accompanying drawings.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention will be indicated in the claims.

BRIEF DESCRIPTION OF THE DRAWING FIGURES

For a more complete understanding of the invention, reference is made to the following description and accompanying drawings, in which:

FIGS. 16A-16C are front views of the powered toothbrush head of FIG. 15 in various positions generated when in motion;

DETAILED DESCRIPTION OF THE PREFERRED EMBODIMENT

Figure 1A:
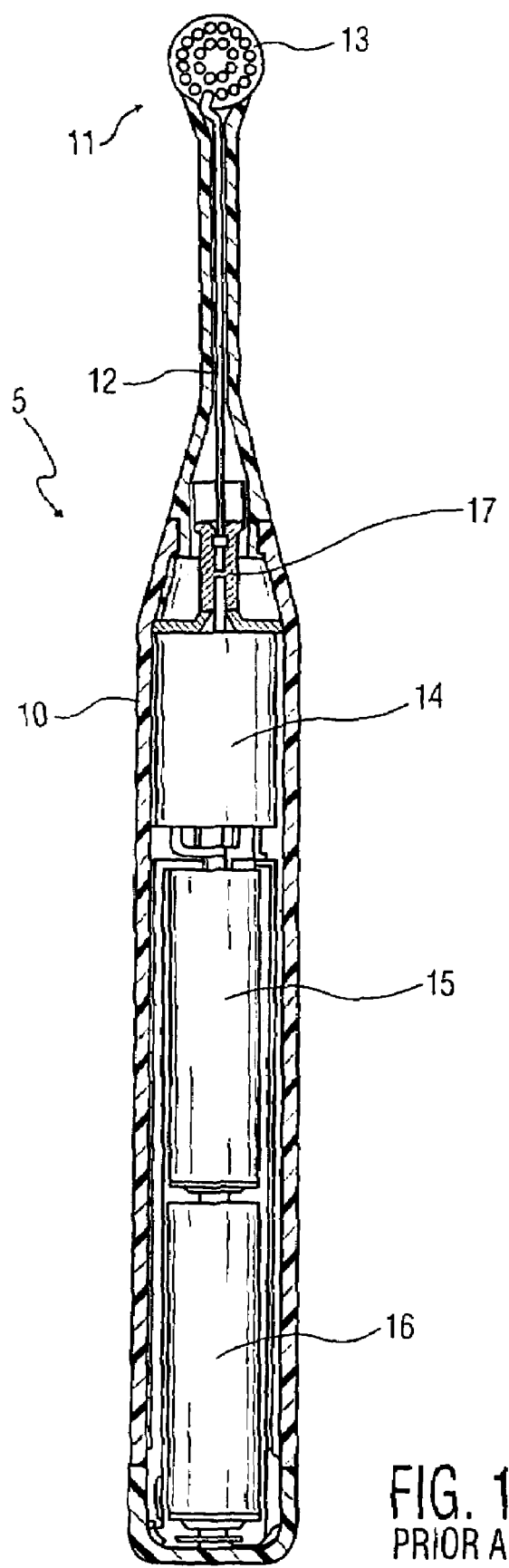
FIG. 1A, is a front partial cross-sectional view of a conventional powered toothbrush including a head.
Figure 1B:
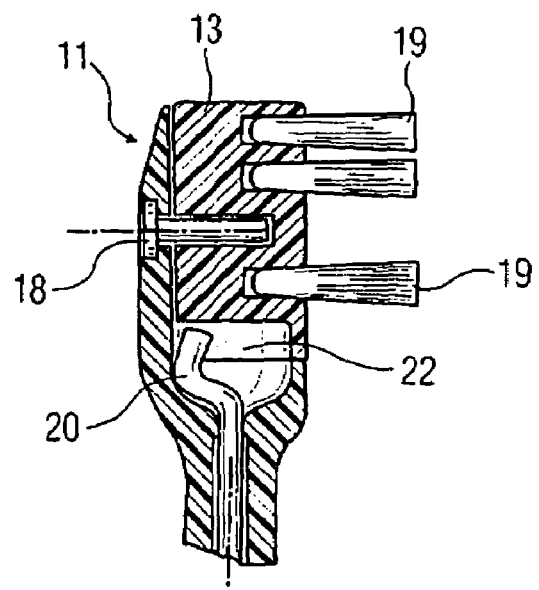
FIG. 1B is a partial side cross-sectional view of toothbrush head of FIG. 1 A.
Figure 1C:
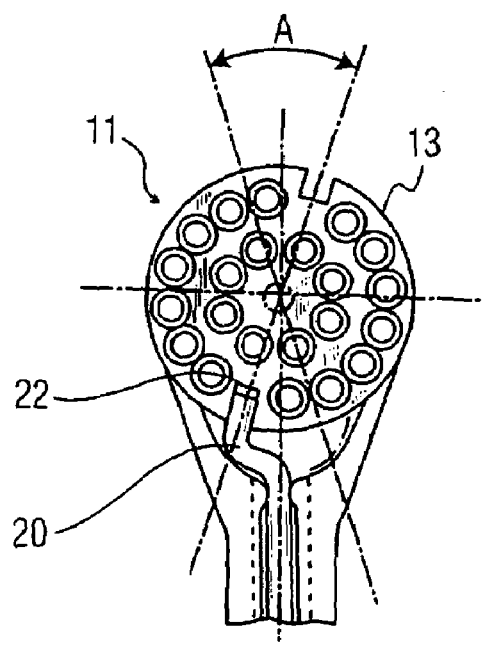
FIG. 1C is a partial front cross-sectional view of toothbrush head of FIG. 1A.
Figure 2:
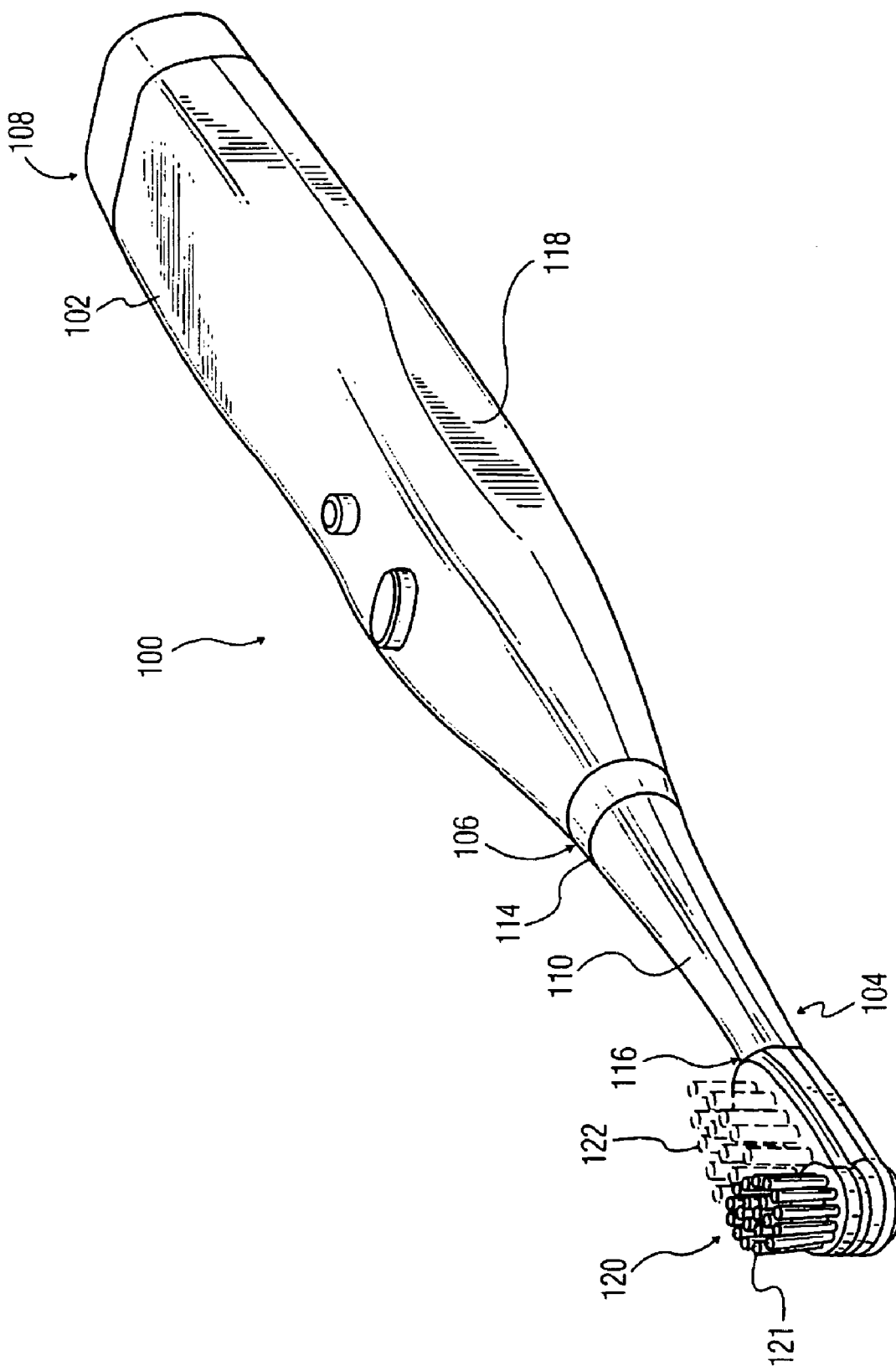
FIG. 2 is a front and side perspective view of a powered toothbrush according to one exemplary embodiment of the invention showing a toothbrush head having distinct first and second movable sections constructed in accordance with the invention.

Referring first to FIG. 2, an exemplary powered toothbrush according to a first embodiment of the invention is illustrated and generally indicated at 100. Toothbrush 100 includes a handle 102 at a proximal end thereof that defines an interior compartment (not illustrated) for housing various toothbrush components, and a brush section 104 that is defined by a neck 110 that terminates in a head 120 at a distal end of toothbrush 100. Handle 102 has a free proximal end 108 and an opposite neck end 106. Neck 110 generally includes a first end 114 and a second end 116 with first end 114 being located at neck end 106 of handle 102 and the second end 116 being located at head 120. In other words, neck 110 is the portion of toothbrush 100 that extends between handle 102 and head 120. Neck 110 also defines an interior compartment (not shown) for housing various working components of toothbrush 100. Head 120 is preferably generally aligned with the longitudinal axis of toothbrush 100.

Neck 110 and handle 102 may be constructed as a unitary member by forming neck 110 integral to handle 102 at neck end 106 of handle 102, or may be formed detachable from handle 102 at neck end 106 of neck 110. In accordance with this detachable embodiment, the combined neck 110 and head 120 can be removed from handle 102 to permit cleaning, servicing and/or interchanging of either handle 102 or the combined neck 110 and head 120 (brush section 104). When neck 110 is formed to be detachable from handle 102, first neck end 114 preferably includes a connector linkage (not illustrated) that is adapted to be detachably joined to handle 102 using traditional techniques. It will also be appreciated that the point of detachment may be between head 120 and neck 110 such that head 120 is of a refill head type. Furthermore, head 120 is formed of a first bristle carrier 121 and a second bristle carrier 122.

It will further be appreciated that the illustrated shapes of handle 102 and neck 110 are merely exemplary in nature and handle 102 and/or neck 110 can be formed to have any number of shapes. Preferably, the shapes of handle 102 and neck 110 are ergonomically pleasing to a user of toothbrush 100 and provide a toothbrush that is easily gripped and held and easily manipulated by the user. For example, handle 102 may include slightly recessed finger sections 118 which are formed on opposite sides of handle 102. One recessed finger section 118 is designed to receive the thumb of one hand and the other recessed finger section 118 is designed to receive one or more other fingers of the same hand to thereby assist the user in proper placement of toothbrush 100 in the user's hand. One or more of recessed finger sections 118 may include ribs or another type of roughened surface to assist the user in gripping toothbrush 100 at recessed finger sections 118.

Figure 3:
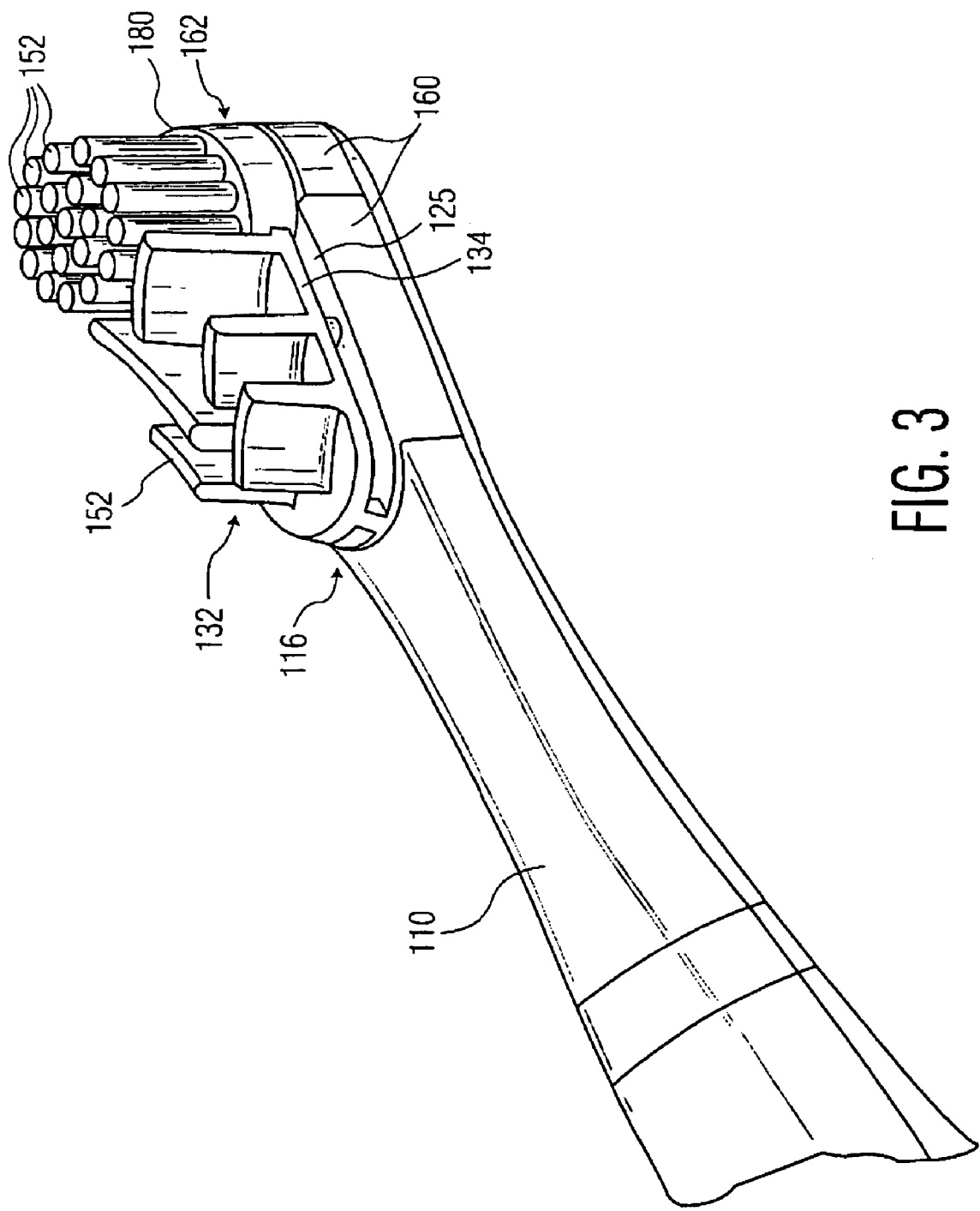
FIG. 3 is a front and side perspective view of a powered toothbrush head according to another exemplary embodiment of a powered toothbrush constructed in accordance with the invention.
Figure 4:
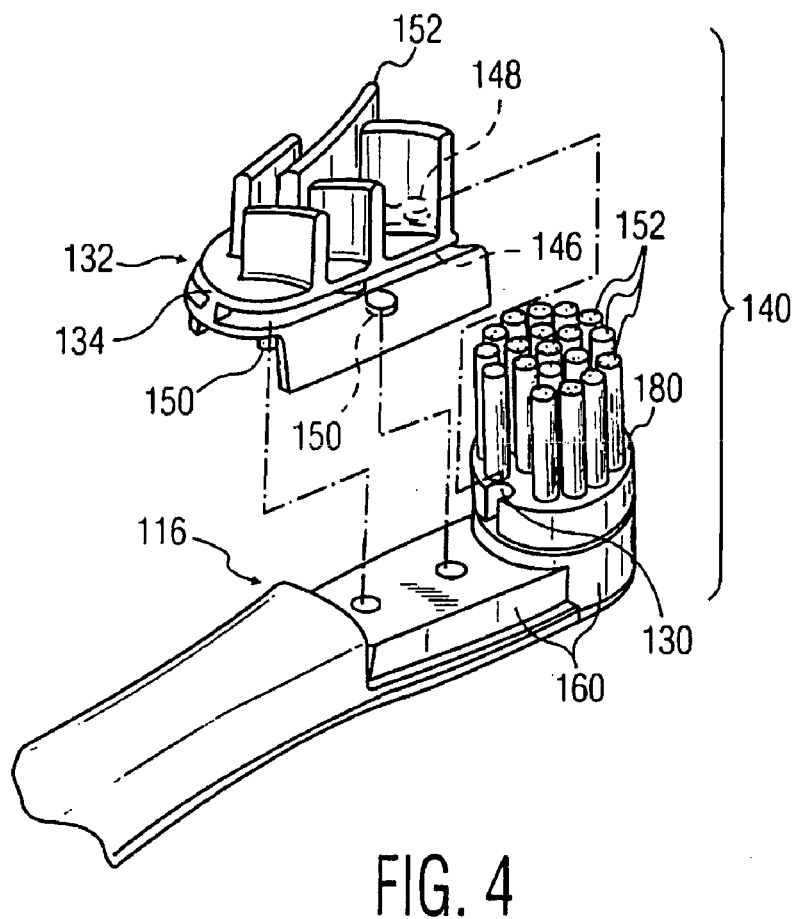
FIG. 4 is a front and side perspective exploded view of the powered toothbrush head of the powered toothbrush of FIG. 3.
Figure 5:
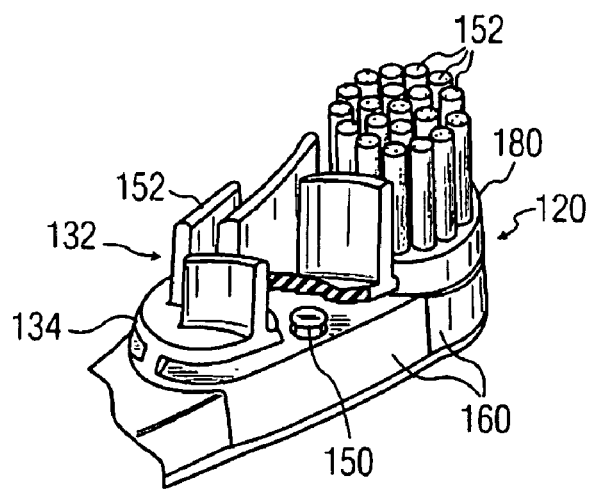
FIG. 5 is a front and side perspective cutaway view of the powered toothbrush head of the powered toothbrush of FIG. 3.

Referring next to FIGS. 3-5, an additional embodiment of a powered toothbrush head is shown. A head 120 of toothbrush 100 includes a head base 160 that partially defines an inner compartment 125 of head 120. Head base 160 may be constructed so that it terminates in a rounded distal end 162, which also defines the distal end of toothbrush 100. Preferably, head base 160 is integrally attached to second end 116 of neck 110.

Head 140 also includes a first movable bristle carrier 180 which is illustrated as being at the outermost or distal portion of head 140. First bristle carrier 180 may have a construction that is either identical to or similar to that of the bristle holders 13 or 121 illustrated in FIGS. 1A-1C and FIG. 2. First movable bristle carrier 180 is preferably formed with a disk having circular cross-section since it is intended to oscillate in a rotational manner about a center point thereof; first movable bristle carrier 180 is formed defining a recess 130 directed toward a second movable bristle carrier 132. However, it will be appreciated that first movable bristle carrier 180 is not limited to having a disk shape and can have any number of different shapes, such as an oval or various other regular or irregular shapes, so long as first moveable bristle carrier 180 is able to oscillate in a substantially rotational manner. A circular shape is preferred since it requires the least amount of clearance to accommodate the oscillating movement.

A plurality of tooth care elements 152 are coupled to and extend outwardly from first movable bristle carrier 180 in a direction substantially perpendicular to a plane defined by a face of first movable bristle carrier 180. As used herein, the term "tooth care elements" includes any type of structure that is commonly used or is suitable for use in providing oral health benefits (e.g., tooth cleaning, tooth polishing, tooth whitening, etc.) by making intimate contact with surfaces of the teeth and surrounding areas. Such tooth care elements include but are not limited to tufts of bristles that can be formed to have a number of different shapes and sizes, and various elastomeric members (see FIGS. 19A-19E) that can be formed to have a number of different shapes and sizes, or a combination of both. Bristle tufts arranged on first bristle carrier 180 is only one exemplary configuration and it will be understood that other bristle configurations (such as stapled, IMT, etc.) can be used. Bristle tufts may all be formed of the same or different bristle materials (such as nylon bristles, spiral bristles, rubber bristles, etc.) Moreover, while the tooth care elements can be arranged so that they are generally perpendicular to the face of first bristle carrier 180 (as noted above), some or all of the tooth care elements can be angled at various angles with respect to first bristle carrier 180 as desired. When first bristle carrier 180 includes bristle tufts, it is thereby possible to select the combination of bristles configurations, bristle lengths, bristle materials and bristle orientations to achieve specific intended results, such as to create as much movement from the moving tuft heads to deliver additional oral health benefits such as enhanced cleaning, tooth polishing and/or tooth whitening.

While first bristle carrier 180 has been defined as a movable bristle carrier 180, it will be understood that first movable carrier 180 is not limited to having only tufts of bristles as a part thereof. Instead, first movable carrier 180 is to be broadly considered as being a carrier for any number of suitable tooth care elements 152 or any number of combinations of different types of tooth care elements 152. For example, first movable carrier 180 may include a number of elastomeric members to provide the desired oral health benefits. The elastomeric members may be attached to first movable carrier 180 using conventional techniques, including integrally forming the elastomeric members with an upper surface of carrier 180. Tooth care elements 152 provided as part of first movable carrier 180 can thus be entirely of one type (e.g., bristle tufts or elastomeric members) or can be formed according to a mixed arrangement.

Figure 19A:
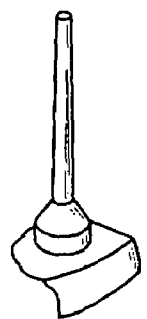
FIG. 19A is a perspective view of an elastomeric tooth care element having a first configuration and adapted for use in a toothbrush head constructed in accordance with the invention.
Figure 19B:
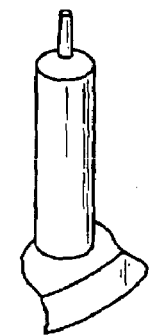
FIG. 19B is a perspective view of an elastomeric tooth care element having a second configuration and adapted for use in a toothbrush head constructed in accordance with the invention.
Figure 19C:
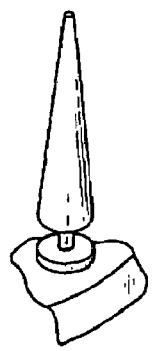
FIG. 19C is a perspective view of an elastomeric tooth care element having a third configuration and adapted for use in a toothbrush head constructed in accordance with the invention.
Figure 19D:
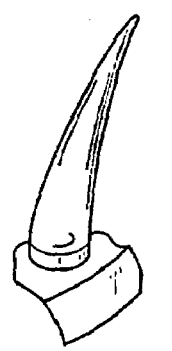
FIG. 19D is a perspective view of an elastomeric tooth care element having a fourth configuration and adapted for use in a toothbrush head constructed in accordance with the invention.
Figure 19E:
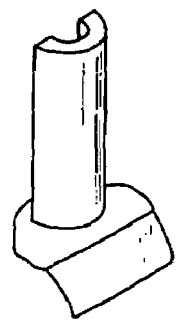
FIG. 19E is a perspective view of an elastomeric tooth care element having a fifth configuration and adapted for use in a toothbrush head constructed in accordance with the invention.

FIGS. 19A-19E illustrate various exemplary elastomeric members that may serve as tooth care elements 152. FIG. 19A shows an elastomeric tooth care element in the form of a thin spike; FIG. 19B shows an elastomeric tooth care element in the form of a barrel spike; FIG. 19C shows an elastomeric tooth care element in the form of a squeegee point; FIG. 19D shows an elastomeric tooth care element in the form of an angled point; and FIG. 19E shows an elastomeric tooth care element in the form of a section of an elastomeric wall. The elastomeric wall of FIG. 19E may be formed with a linear, planar shape; a zigzag shape; a serpentine shape, etc. All of the above elastomeric tooth care elements may be formed having smooth textures or can have rough surfaces. In addition, the wall sections of the elastomeric tooth care elements may be formed vertically straight, taper inward toward one end or expand toward one end. The tops of the elastomeric tooth care walls may be formed with a planar surface or a protrusion (i.e., hump) or the like formed thereat.

For purpose of illustration only, first movable carrier 180 will be described as containing a predetermined number of bristle tufts; however the following features apply equally to the situation where first movable carrier 180 is formed entirely or partly of elastomeric members. The bristle tufts of first movable carrier 180 may be formed with uniform heights or non-uniform heights. For example, first movable carrier 180 may include bristle tufts having a first height as well as bristle tufts having a second different height.

First movable bristle carrier 180 is constructed so as to pivotally rotate about a center point thereof, thereby effectuating movement of the bristle tufts and/or elastomeric members that extend outwardly from first movable bristle carrier 180. The movement of first movable bristle carrier 180 is preferably an oscillation type movement as first movable bristle carrier 180 pivots about a post at a center point thereof (see FIG. 1). First movable bristle carrier 180 is formed with a slot or opening (not illustrated). This slot is preferably identical to or substantially similar to slot 22 illustrated in FIGS. 1A-1C. Preferably, slot 22 is formed at a peripheral edge of first movable bristle carrier 180 and extends along a substantial height of first movable bristle carrier 180. For example, slot 22 preferably does not extend to the upper surface of first bristle carrier 180 where the tooth care elements are positioned. Instead, slot 22 preferably has a closed upper end to prevent foreign matter, such as saliva, toothpaste, foreign particles, etc., from entering slot when the operator is performing a brushing operation. The opposite end of slot 22 that is located within the inner compartment 125 of head 140 can be open.

Toothbrush 100 includes a drive mechanism to effectuate movement of certain parts of the toothbrush and more specifically, for causing movement of first movable bristle carrier 180. One exemplary drive mechanism is disclosed in U.S. Pat. No. 5,625,916 to McDougall, which has been previously incorporated herein by reference and includes a rotating drive shaft 200 that extends at least through neck 110 (i.e., the inner compartment thereof). Drive shaft 200 preferably has a construction that is the same as or similar in nature to shaft 12 illustrated in FIGS. 1A-1C.

Drive shaft 200 has one end (not illustrated) that is operatively connected to a drive member (not illustrated), such as a motor or any other type of drive device, for imparting movement to first movable bristle carrier 180. Drive shaft 200 is formed with an opposing distal end (not illustrated) that is bent such that the end is not axially aligned with the longitudinal axis of drive shaft 200. This distal end may be formed similar to the end 20 of FIGS. 1A-1C or may be formed differently so long as it performs the intended function. In other words, the end is an offset crank end of drive shaft 200 and is configured to be received in slot 22 so that a 360° rotational movement of shaft 200 is transmitted into an oscillating back and forth rotational movement of first movable bristle carrier 180.

The drive mechanism for powered toothbrush 100 can be any type of drive, e.g., a rotating drive, an oscillating drive, an eccentric drive, an unbalanced-generated drive, a drive having one more gearing mechanisms, and/or the like, that is capable of performing the intended function. The drive mechanism can be realized in the form of an electric motor or other type of motor and the movement generated by the drive can be imparted to one or more sections of head 140 (or 120) or to other elements that can be present at the brush section, such as bristle tufts, elastomeric members. The movement can be imparted directly through a driving axle, such as drive shaft 200 or it can be imparted through a driving post attached to the driving axle. When toothbrush 100 includes an oscillating drive mechanism either identical to or similar to the exemplary drive mechanism illustrated in FIGS. 1A through 1C, the interior compartment of handle 102 houses a motor operatively connected to drive shaft 200 and a source to power the motor, such as one or more batteries.

When the drive mechanism is actuated and drive shaft 200 is rotated, the movement of the crank end thereof imparts an oscillating back and forth movement of first movable bristle carrier 180 through an angle between about 10° to about 120° and in a preferred exemplary embodiment, the movement is through an angle between about 10° to about 30°, and in a most preferred embodiment is through an angle between about 10° to about 15°.

Figure 6C:
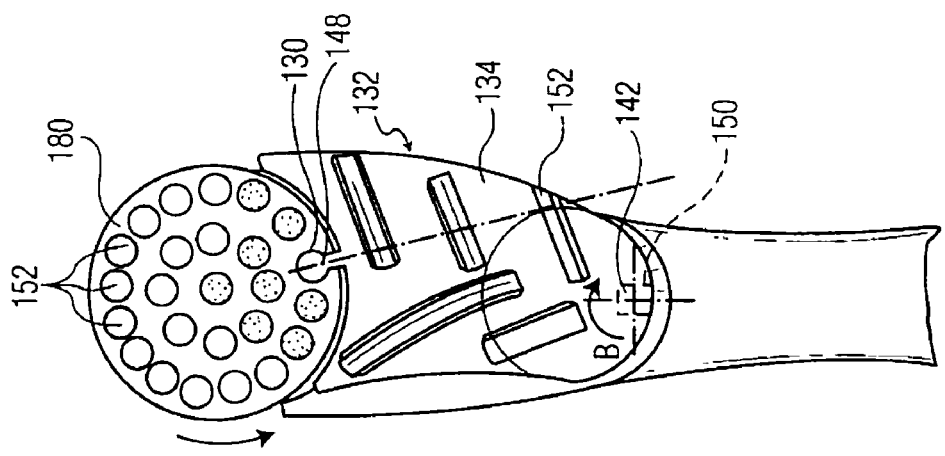
FIGS. 6A-6C are front views of the powered toothbrush head of FIG. 3 in various positions generated when in motion.
Figure 6B:
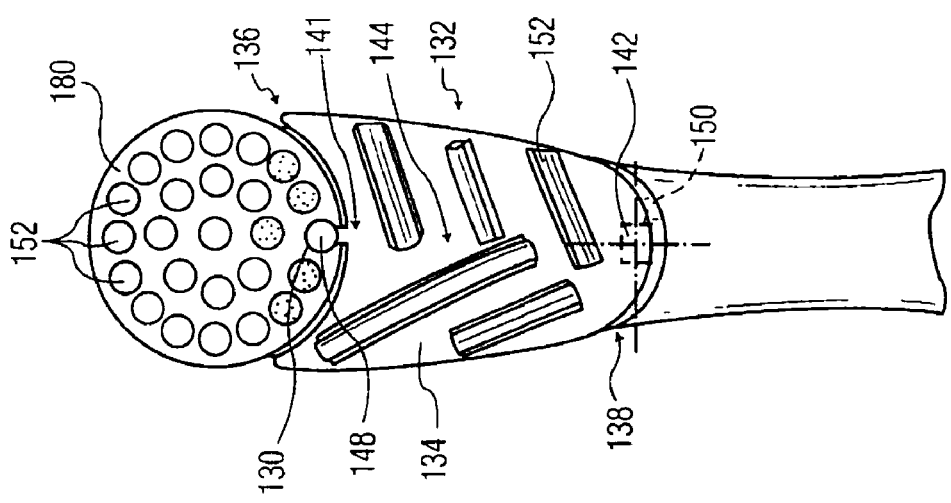
Figure 6A:
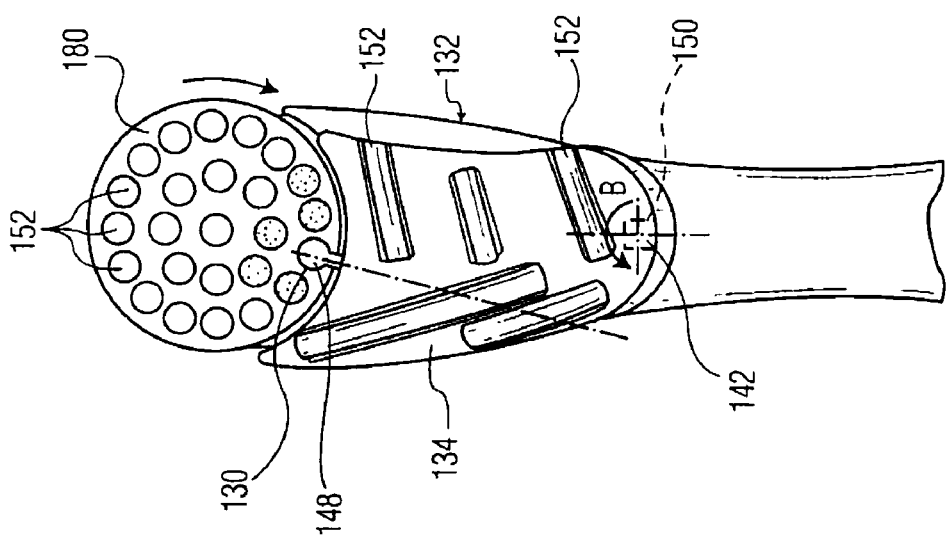

Referring next to FIGS. 6A, 6B and 6C in addition to FIGS. 3-5. toothbrush 100 (and head 140) further includes a second movable bristle carrier 132 that is operably mounted on head 140. Second movable bristle carrier 132 comprises a platform 134 having a first end 136, a second end 138, a first end midpoint 141, a second end midpoint 142, a midpoint 144, and a bottom 146. A protrusion 148 extends outwardly from platform 134 at first end 136 thereof and is received into recess 130 of first movable bristle carrier 180, thereby providing a link between the first movable bristle carrier 128 and the second movable bristle carrier 132. In a preferred embodiment a feature, such as at least one leg 150 is formed integral with platform 134 and is adapted to be received by head base 160 to support platform 134. It will be understood that at least one leg 150 can have a number of different shapes and broadly, any member that can act as a support member can be used to couple platform 134 to head base 160.

There are numerous portions of the present invention, that when changed in accordance with various embodiment of the invention, will change the type and range of motion of both first movable bristle carrier 180 and second movable bristle carrier 132. The movement of first movable bristle carrier 180 outlined above and can be altered by varying the drive or transmission of the motion of that drive to first movable bristle carrier 180. These variations are well known in the art.

Because movement of first movable bristle carrier 180 directly imparts movement to the platform 134 changes to the movement of first movable bristle carrier 180 will also change the movement of second movable bristle carrier 132. Additionally, changes in the structure and anchoring of second movable bristle carrier 132 can vary its movements as well. Various embodiments may be designed so that protrusion 148 of platform 134 is rigidly received in recess 130, or protrusion 148 may be frictionally received in recess 130.

Other changes to second movable bristle carrier may include that legs 150 and platform 134 may be formed from either a rigid or an elastomeric material. Different combinations of rigid or elastomeric legs 150 and platforms 134 will result in varied types and ranges of motion of platform 134. Another factor that will affect the type and range of the motion of platform 134 is the placement and number of the legs 150. In one of the preferred embodiments of the present invention, illustrated in FIGS. 6A-6C, is included one leg 150 formed integral platform 134 at about the second end midpoint 142 thereof. The movement of first movable bristle carrier 180 imparts a torsional movement on leg 150, as shown by arrow B and rotates platform 134 as well as imparts a lateral shift of first end 136 of second movable bristle carrier 132 parallel to the first end 136.

In other embodiments of the present invention, a first leg 150 is formed integral with platform 134 at the first end midpoint 141 thereof and/or a second leg 150 is formed integral with platform 134 at second end midpoint 142, as illustrated in FIGS. 3 through 5. A leg 150 may also be formed integral with platform 134 at midpoint 144 thereof, alone or in combination with other legs 150, as illustrated in FIGS. 7 through 10.

Figure 7:
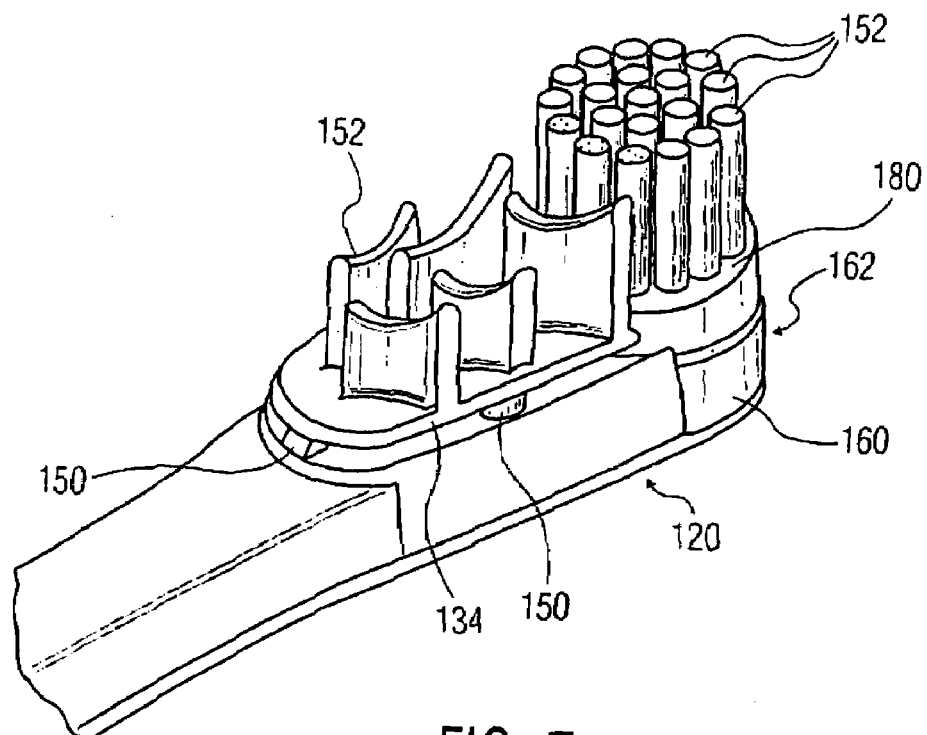
FIG. 7 is a front and side perspective view of another embodiment of a powered toothbrush head of the powered toothbrush of FIG. 2.
Figure 8:
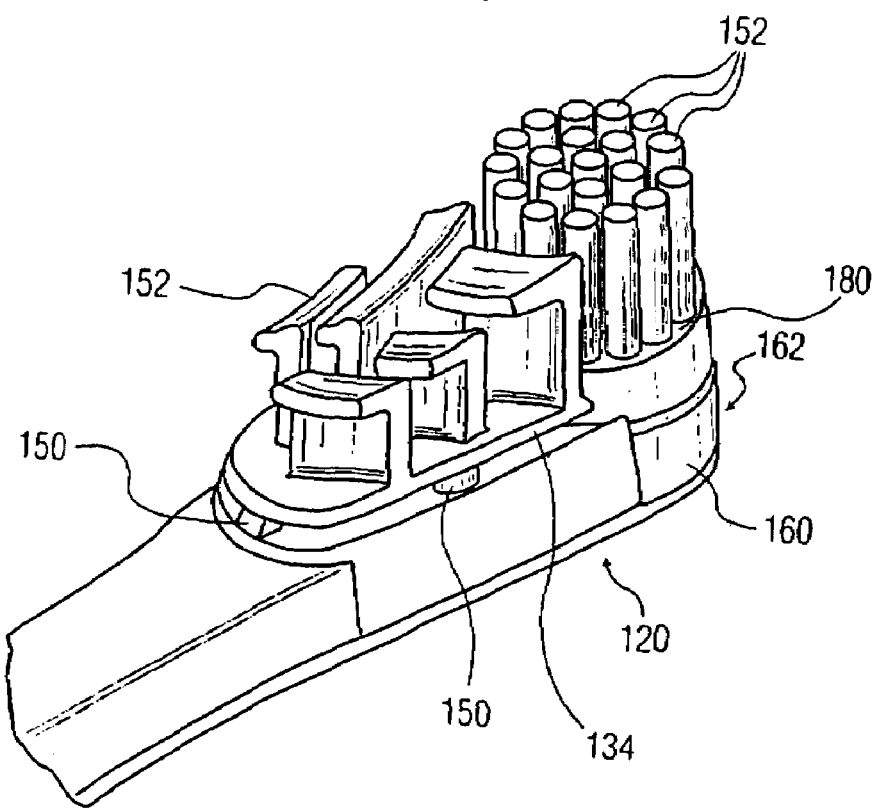
FIG. 8 is a front and side perspective view of another embodiment of a powered toothbrush head of the powered toothbrush of FIG. 2.
Figure 9:
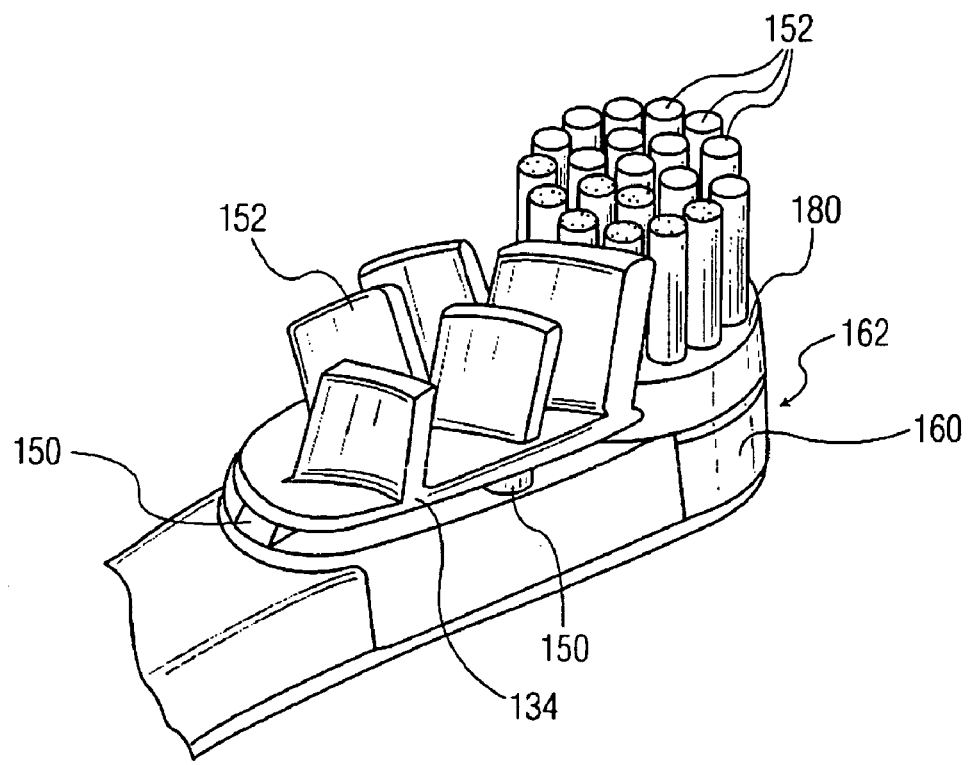
FIG. 9 is a front and side perspective view of another embodiment of a powered toothbrush head of the powered toothbrush of FIG. 2.
Figure 10:
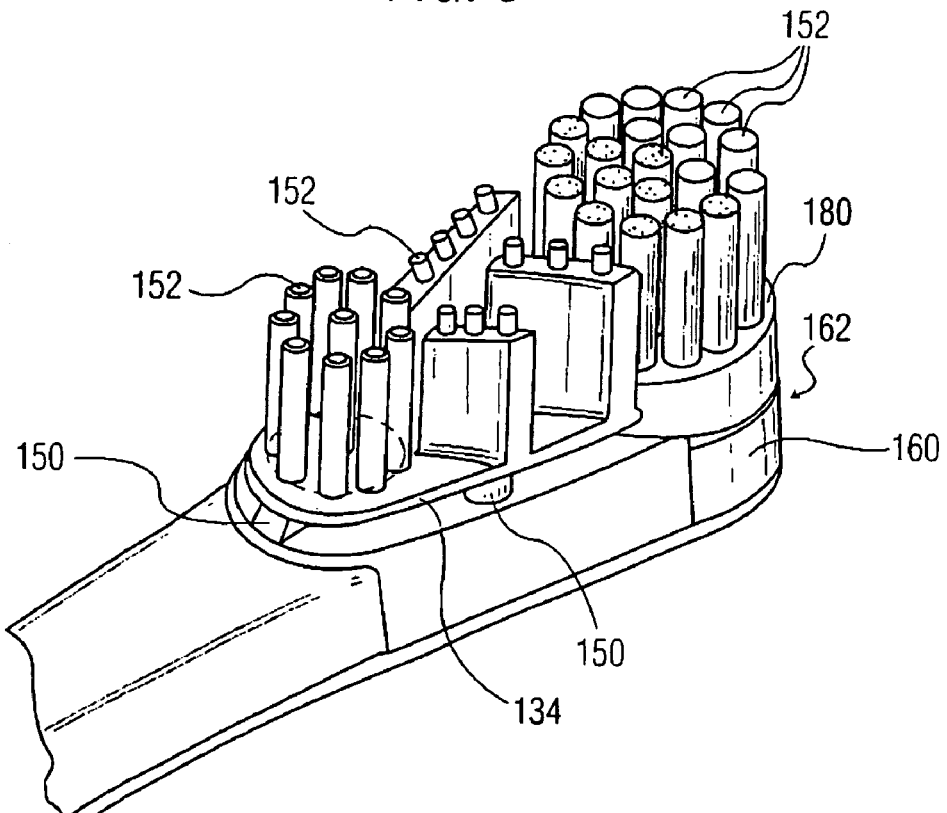
FIG. 10 is a front and side perspective view of another embodiment of a powered toothbrush head of the powered toothbrush of FIG. 2.

FIGS. 3-10 also illustrate differing variations and combinations of tooth care elements 152 including bristles and elastomeric tooth care elements. FIGS. 3-5 illustrate second movable bristle carrier being formed with short elastomeric walls in varying sizes and placement. FIG. 7 illustrates second movable bristle carrier being formed with short elastomeric walls having a top surface thereof being cupped. FIG. 8 illustrates second movable bristle carrier being formed with short elastomeric walls being formed with an overhang. FIG. 9 illustrates second movable bristle carrier being formed with short elastomeric walls that are not all erected parallel, but lean or curve to one side. Referring next to FIG. 10, the second movable bristle carrier contains a combination of short elastomeric walls with humps and a lower bristle section. The above variations are for illustration purposes only and it is realized that any combination of tooth care elements may be employed.

Figure 11:
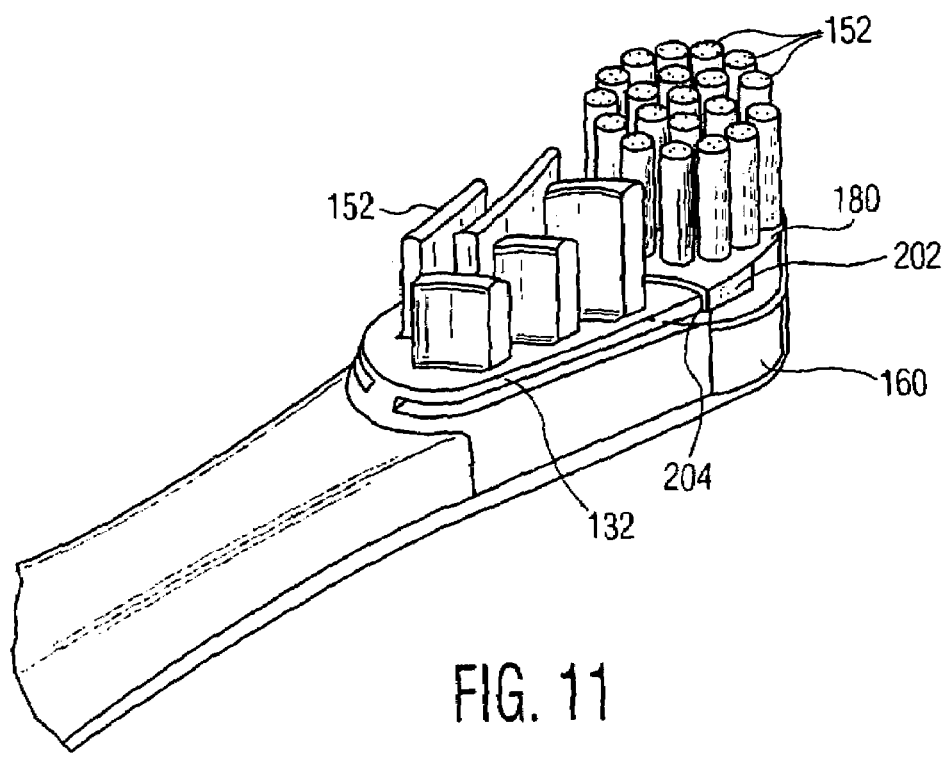
FIG. 11 is a front and side perspective view of another embodiment of a powered toothbrush head of the powered toothbrush of FIG. 2.
Figure 12:
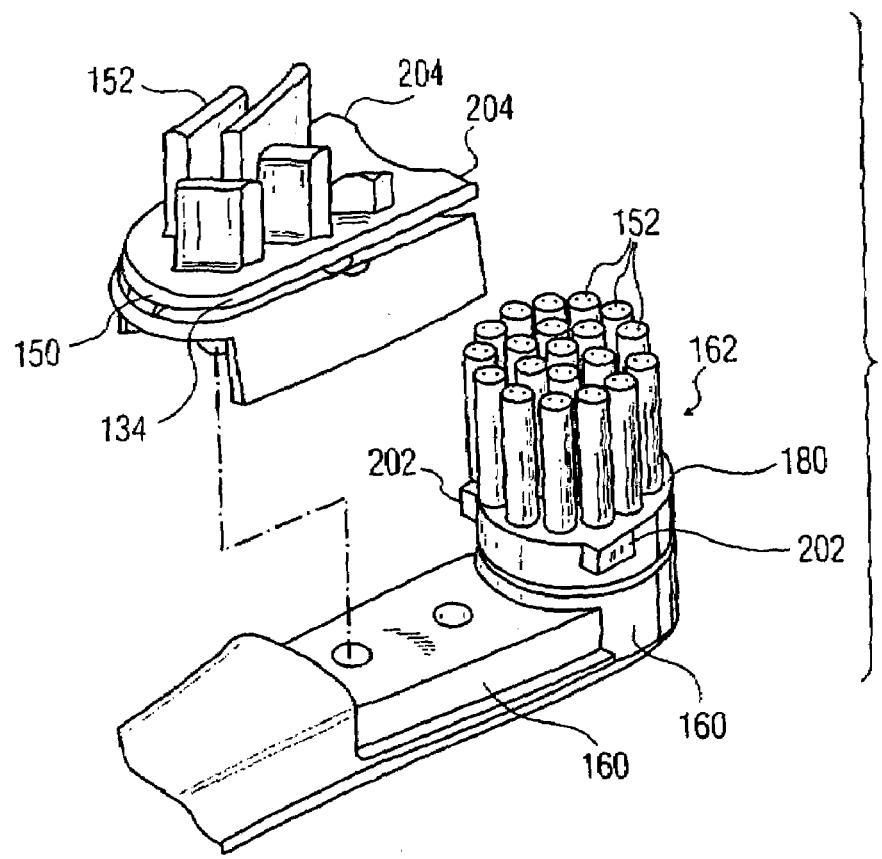
FIG. 12 is a front and side perspective exploded view of the embodiment of the powered toothbrush head of FIG. 11 of the powered toothbrush of FIG. 2.
Figure 13:
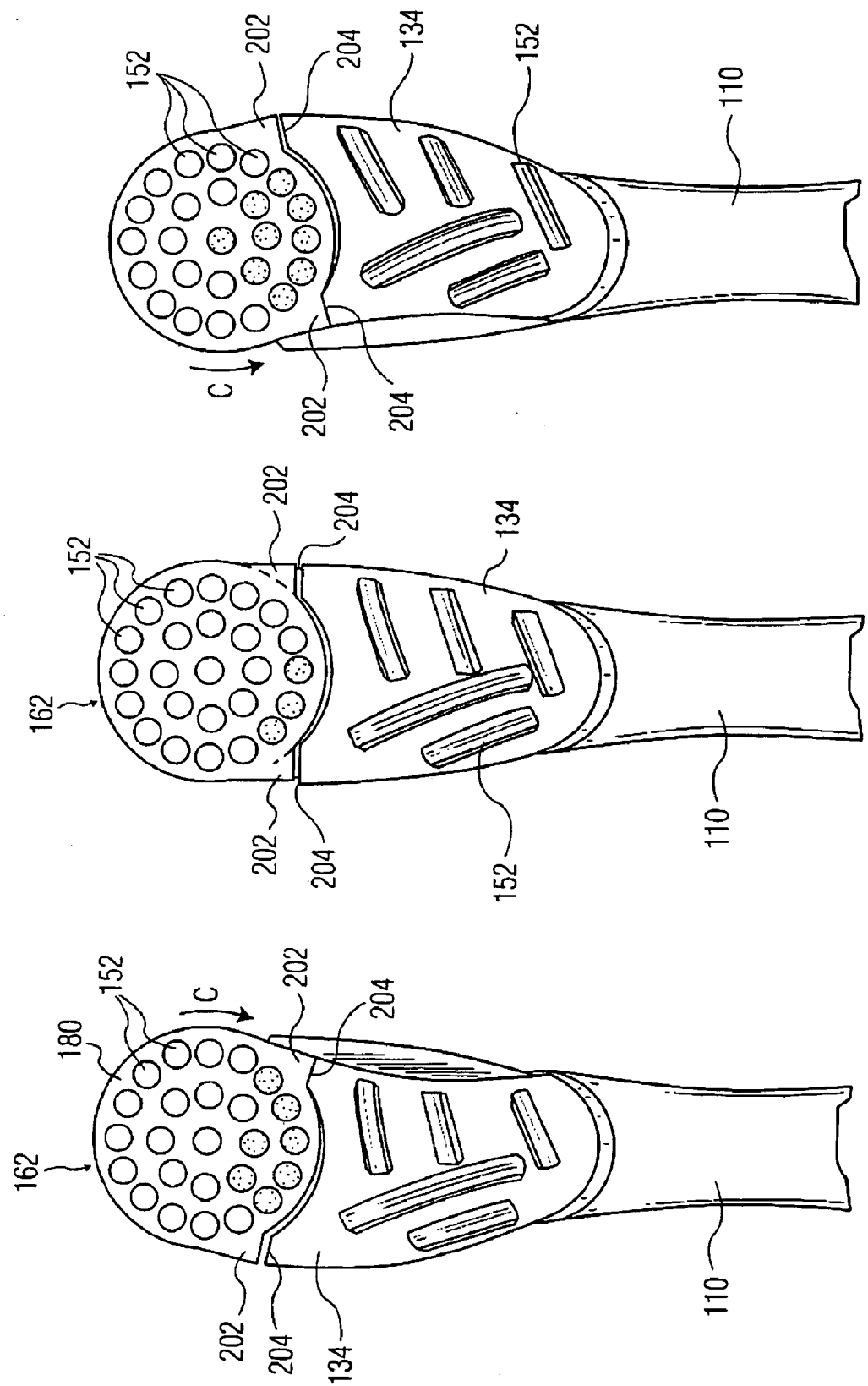
FIGS. 13A-13C are front views of the powered toothbrush head of FIG. 11 in various positions generated when in motion.

FIGS. 11 through 13 illustrate an alternative embodiment of the invention utilizing head construction. The handle 102, neck 110, drive and head base 160 may be formed similarly as described above. However in accordance with this embodiment of the invention first movable bristle carrier 180 is formed with one or more protrusions 202 directed toward plant 134 of second movable bristle carrier 132.

Figure 14:
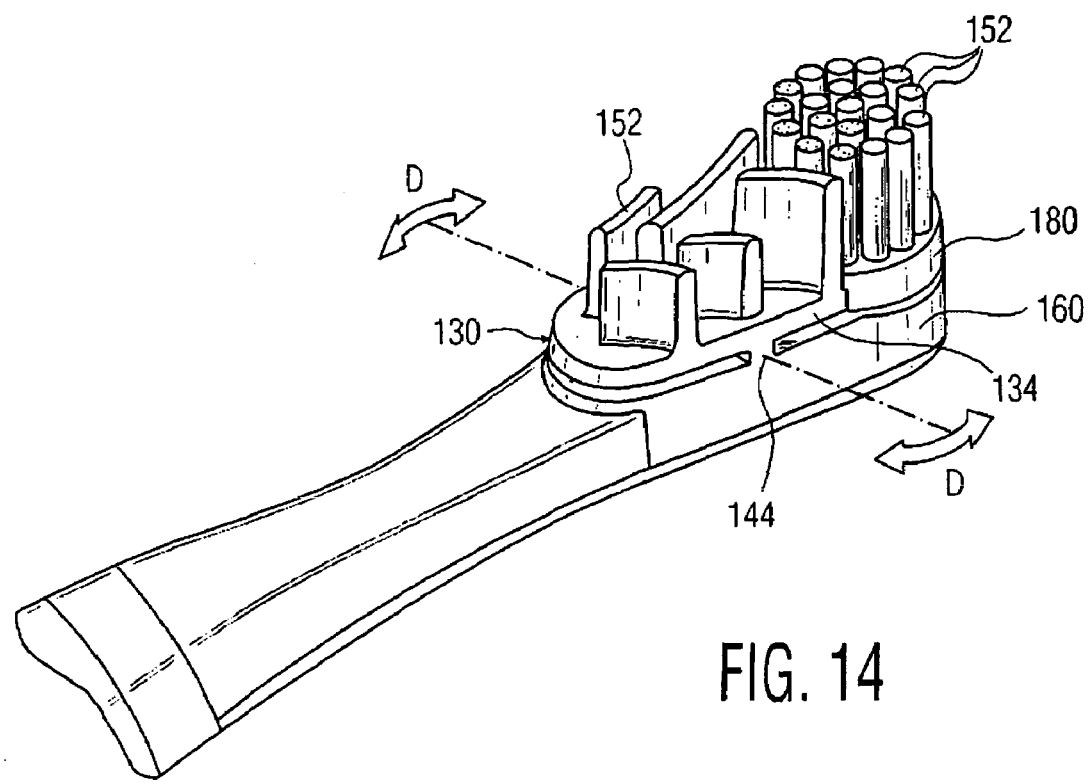
FIG. 14 is a front and side perspective view of another embodiment of a powered toothbrush head of the powered toothbrush of FIG. 2.
Figure 15:
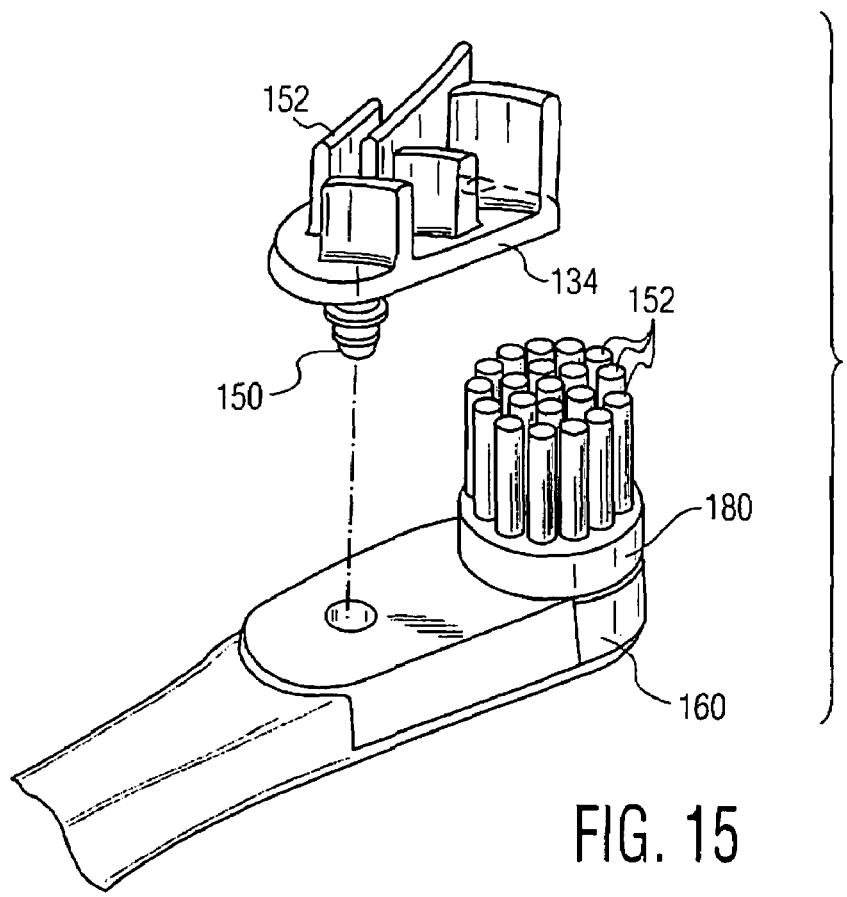
FIG. 15 is a front and side perspective view of another embodiment of a powered toothbrush head of the powered toothbrush of FIG. 2.

FIGS. 14 through 16 illustrate additional exemplary embodiments generating various movements. FIG. 14 illustrates the movement of platform 134 when the leg 150 is located solely at the midpoint 144 of platform 134. Platform 134 will therefore rotate along arrow D, this will impart greater movement to second end 138 of platform. FIG. 15 illustrates an embodiment where leg 150 is pivotally connected to base 160. This will again allow greater movement of second end 138. The above movements will be generated regardless of how the motion from first movable bristle carrier 180 is imparted to platform 134. FIGS. 16A-16C illustrate various positions generated during movement of the constructions illustrated in FIGS. 14 and 15. Both of these constructions include second movable bristle carriers that may rotate about the midpoint 144 thereof, resulting in an increase in the lateral movement of second end 138 of platform 134, as illustrated by arrow E, when first movable bristle carrier 180 oscillates across arrow F.

Figure 17:
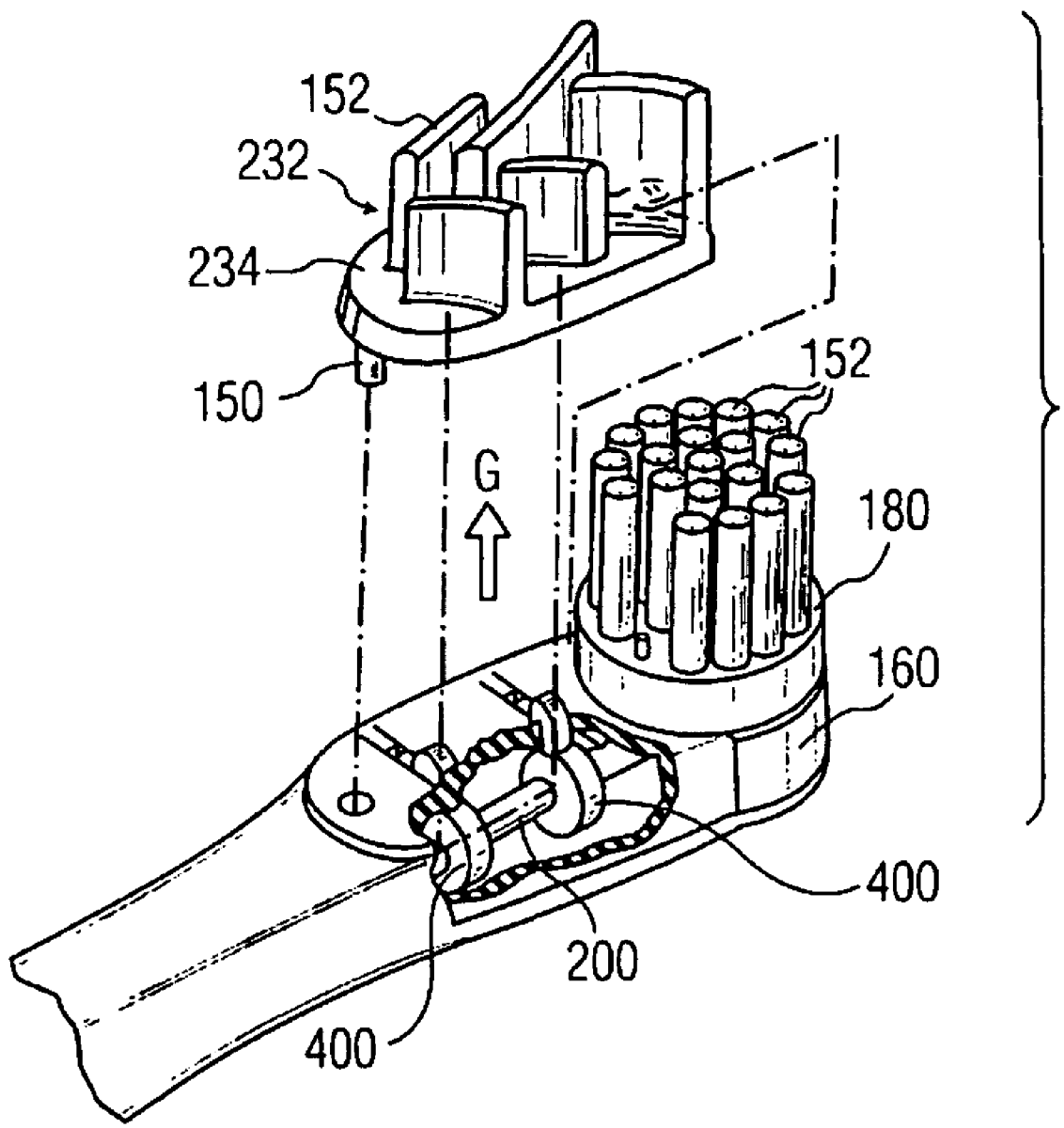
FIG. 17 is a front and side exploded cut-away perspective view of another embodiment of a powered toothbrush head of the powered toothbrush of FIG. 2.
Figure 17A:
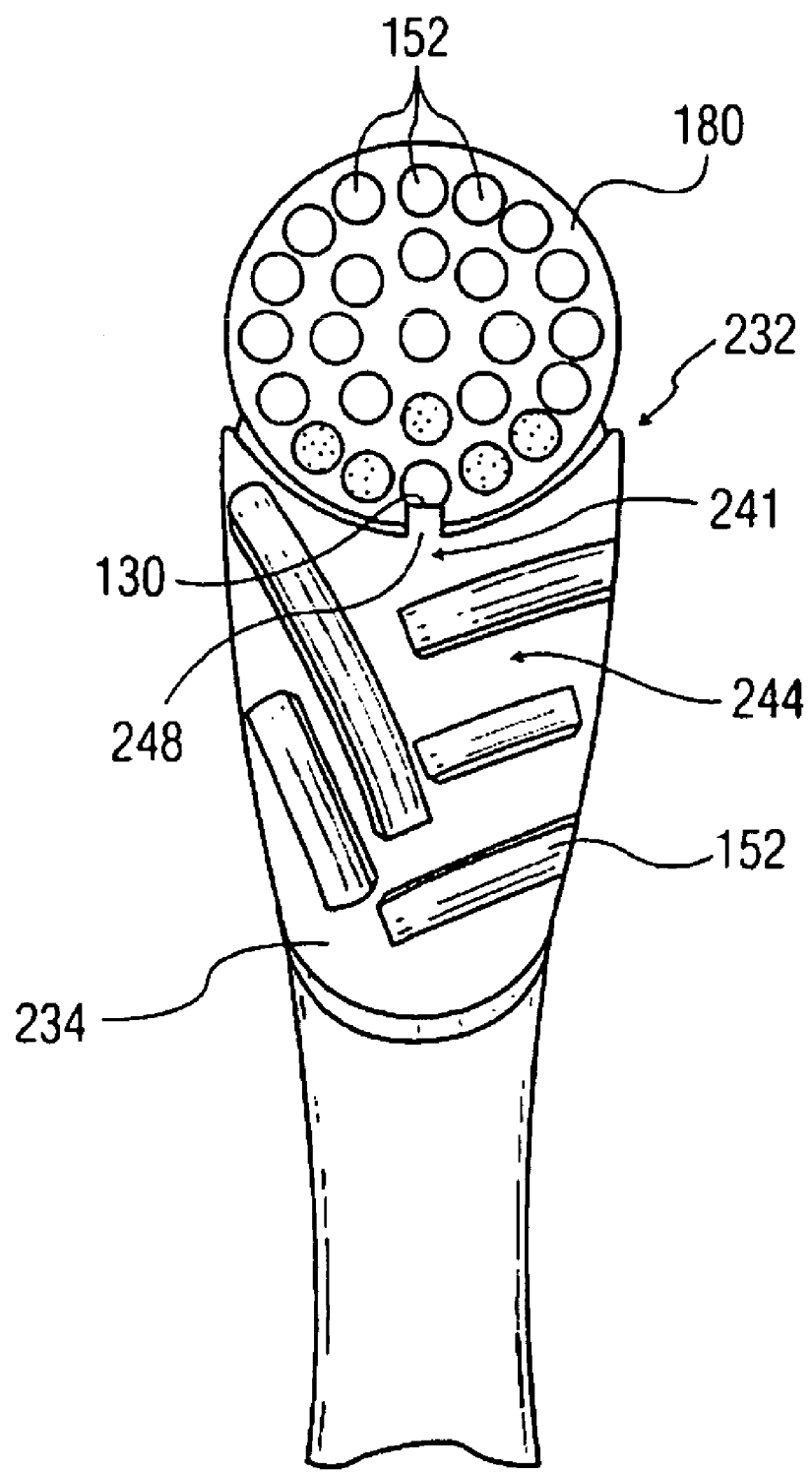
FIG. 17A is a front view of the powered toothbrush head of FIG. 17 in accordance with one embodiment of the present invention.

FIGS 17 and 17A illustrate another exemplary head embodiment. Handle 102, neck 110, drive, and head base 160 may be the same as described above. Similarly, the connection between the first movable bristle carrier 180 and a second movable bristle carrier 232 may be the same as discussed above with reference to any of FIGS. 6A-16. In the illustrated embodiment, a second movable bristle carrier 232 may comprise a protrusion 248 that extends outwardly from a platform 234 at a first end 136 and is received into a recess 130 of the first movable bristle carrier 180. The second movable bristle carrier 232 may additionally be operably connected to a second drive mechanism that will move second movable bristle carrier 232 in a third direction. The second drive feature may include at least one cam surface 400 that selectively contacts second movable bristle carrier 232 or platform 234 to cause movement, in one preferred embodiment, perpendicular to first movable bristle carrier 180 (in the direction indicated by arrow G).

Figure 18:
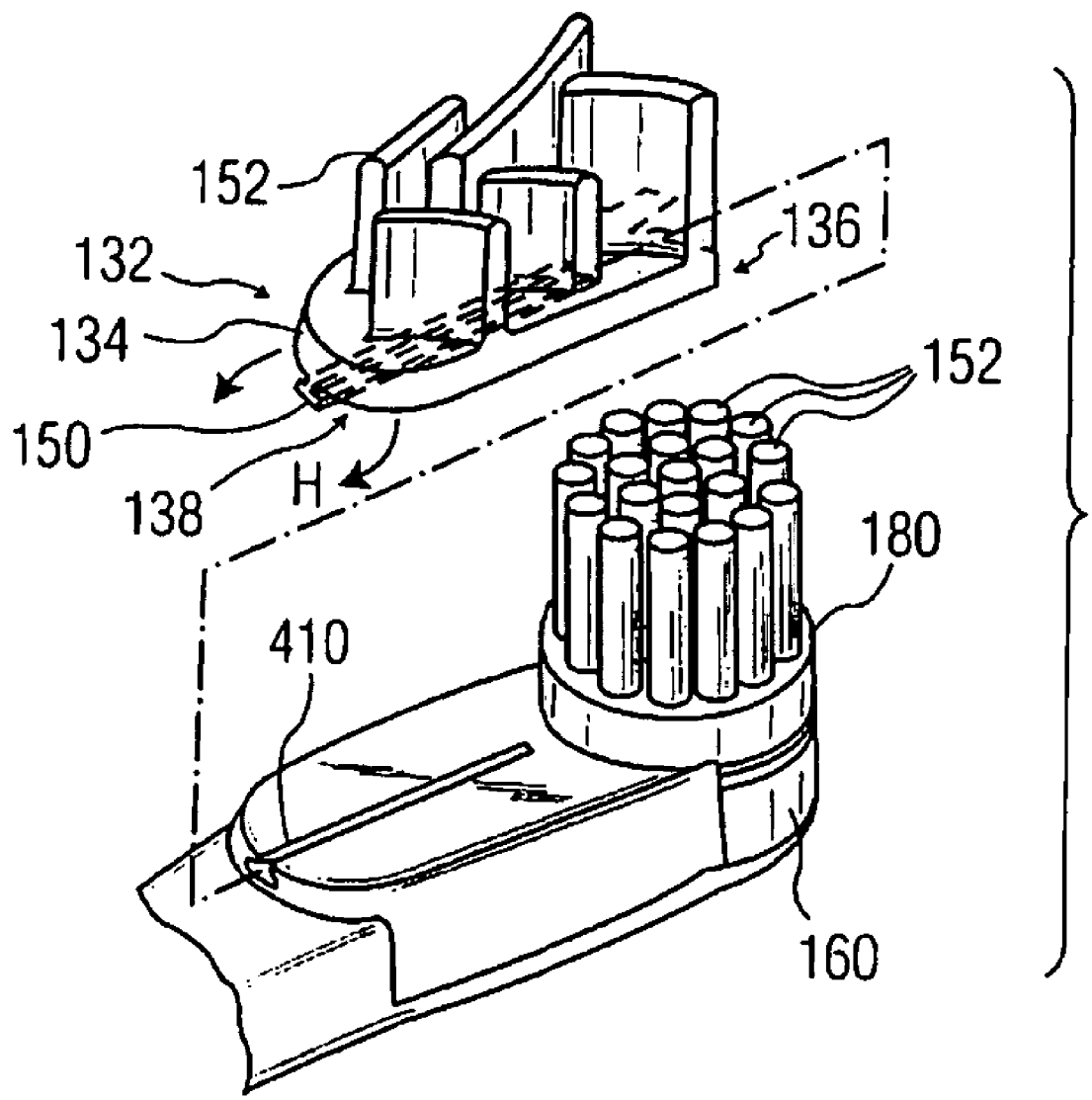
FIG. 18 is a front and side perspective exploded view of another embodiment of a powered toothbrush head of the powered toothbrush of FIG. 2.

FIG. 18 illustrates yet another embodiment wherein leg 150 may span from approximately second end 138 to approximately first end 136 of platform 134. This positioning of leg 150 may cause platform 134 to 'rock' back and forth across the longitudinal axis of toothbrush 100, in the directions indicated by arrows H. Leg 150 may also be attached to second movable bristle carrier 132 via a receiving groove 410.

A powered toothbrush made in accordance with any of the present embodiments offers a number of advantages over conventional powered toothbrushes that are presently available. First movable bristle carrier 180 oscillates back and forth, or moves otherwise. As the operator brushes his or her teeth, the oscillating tooth care elements (i.e., bristle tufts and/or elastomeric members) contact the surfaces of the teeth and the surrounding areas to deliver enhanced cleaning, tooth polishing and/or tooth whitening. The elastomeric second bristle carrier 132 permits a number of additional tooth care elements to be disposed in a number of different patterns. The increased number of moving tooth care elements of second bristle carrier provides increased contact with gingival tissues and enhanced massaging thereof.

The toothbrush according to the various embodiments disclosed herein can be made from any number of materials that are suitable for use in oral care products, such as toothbrushes, etc. For example, many of the components that are included in toothbrush are formed of plastic materials. Accordingly, the handle and head of the powered toothbrush may be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide 2 or polyamide 6), polyesters (for example polyester ester or polyether ester), polyurethanes (for, example polyesterurethane, polyetherurethane or polyesteretherurethane).

It will thus be seen that the objects set forth above, among those made apparent from the preceding description, are efficiently attained and, because certain changes may be made in carrying out the above method and in the constructions) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A powered toothbrush comprising:
    a handle portion having a neck formed at one end; and
    a head coupled to the neck and including:
        a first carrier coupled to the head and having at least one of a plurality of bristles and a cleaning member extending outwardly therefrom, the carrier operatively connected to a first drive for moving the first carrier relative to the head between a first position and a second position; and
        a second carrier coupled to the head at a second end of the second carrier, the second carrier having an upper surface and at least one of bristles and a cleaning member extending outwardly from the upper surface, the second carrier having a first configuration,
    wherein the first carrier engages with a first end of the second carrier between the first position to the second position and deforms the second carrier into a second configuration.

2. The powered toothbrush of claim 1, wherein the first carrier is distal to the second carrier with respect to the handle.

3. The powered toothbrush of claim 2, wherein the second end of the second carrier is proximal to the first end of the second carrier with respect to the handle.

4. The powered toothbrush of claim 1, wherein a convex outer surface of the first carrier engages with a concave surface of the second carrier.

5. The powered toothbrush of claim 4, wherein protrusions on either end of the convex outer surface of the first carrier engage with respective contact points on either side of the concave surface of the second carrier.

6. The powered toothbrush of claim 1, wherein the first carrier rotates about a center axis and imparts a lateral shift of the second end of the second carrier and a rotational bend of the second carrier between the first and second ends of the second carrier.

7. The powered toothbrush of claim 1, wherein the first end of the second carrier is fixed with respect to the head and the first end of the second carrier is movable with respect to the head.

8. The powered toothbrush of claim 1, wherein the configuration of the at least one of bristles and cleaning member varies between the first and second configuration of the second carrier.

9. The powered toothbrush of claim 1, wherein the second carrier is comprised of an elastomeric material.

10. A powered toothbrush comprising:
    a handle portion having a neck formed at one end; and
    a head coupled to the neck and including:
        a first carrier coupled to the head and having at least one of a plurality of bristles and a cleaning member extending outwardly therefrom, the carrier operatively connected to a first drive for moving the first carrier relative to the head between a first position and a second position; and
        a second carrier coupled to the head at a second end of the second carrier, the second carrier having an upper surface and at least one of bristles and a cleaning member extending outwardly from the upper surface, the second carrier having a first configuration,
    wherein the first carrier is engaged with a first end of the second carrier such that movement of the first carrier to the second position deforms the second carrier into a second configuration.

11. The powered toothbrush of claim 10, wherein the first carrier is distal to the second carrier with respect the handle.

12. The powered toothbrush of claim 11, wherein the second end of the second carrier is proximal to the first end of the second carrier with respect to the handle.

13. The powered toothbrush of claim 10, wherein a convex outer surface of the first carrier engages with a concave surface of the second carrier.

14. The powered toothbrush of claim 13, wherein protrusions on either end of the convex outer surface of the first carrier engage with respective contact points on either side of the concave surface of the second carrier.

15. The powered toothbrush of claim 10, wherein the first carrier rotates about a center axis and imparts a lateral shift of the second end of the second carrier and a rotational bend of the second carrier between the first and second ends of the second carrier.

16. The powered toothbrush of claim 10, wherein the second end of the second carrier is fixed with respect to the head and the first end of the second carrier is movable with respect to the head.

17. The powered toothbrush of claim 10, wherein the configuration of the at least one of bristles and cleaning member varies between the first and second configuration of the second carrier.

18. The powered toothbrush of claim 10, wherein the first and second carriers are continuously engaged.

19. The powered toothbrush of claim 10, wherein the second carrier is comprised of an elastomeric material.

* * * * *